United States Patent [19]

Glazer

[11] Patent Number: 4,624,958
[45] Date of Patent: Nov. 25, 1986

[54] ANTIPROTOZOAL 1,4-DI(P-AMIDINOPHENYL)IMIDAZOLES

[75] Inventor: Edward A. Glazer, Waterford, Conn.

[73] Assignee: Pfizer Inc., New York, N.Y.

[21] Appl. No.: 770,328

[22] Filed: Aug. 28, 1985

Related U.S. Application Data

[62] Division of Ser. No. 484,803, Apr. 14, 1983, Pat. No. 4,546,113.

[51] Int. Cl.$^4$ .............. A01N 43/50; A01N 43/40; C07D 233/64; C07D 233/84
[52] U.S. Cl. ...................... 514/341; 514/381; 514/396; 514/398; 514/400; 514/427; 546/278; 548/254; 548/337; 548/342; 548/346; 548/563
[58] Field of Search .............. 546/278; 548/254, 337, 548/342, 346, 563; 514/341, 381, 396, 398, 400, 427

[56] References Cited

U.S. PATENT DOCUMENTS

| | | | |
|---|---|---|---|
| 2,204,983 | 6/1940 | Ewins et al. | 514/637 |
| 3,652,591 | 3/1972 | Dann | 548/503 |
| 3,689,506 | 9/1972 | Dann | 548/503 |
| 4,244,964 | 1/1981 | Heeres et al. | 514/383 |
| 4,301,166 | 11/1981 | Regel et al. | 514/383 |
| 4,313,950 | 2/1982 | Guzzi et al. | 514/383 |
| 4,353,915 | 10/1982 | Stetter et al. | 514/383 |
| 4,407,808 | 10/1983 | Roantree et al. | 514/383 |
| 4,438,128 | 3/1984 | Wiedemann et al. | 514/383 |
| 4,496,571 | 1/1985 | Yellin et al. | 514/383 |

OTHER PUBLICATIONS

Remington's Pharmaceutical Sciences, 14th edit., 1970, pp. 528–529.
Burger, J. Chem. Educ., 33, No. 8, pp. 362–372, 1956.
Das et al., J. Med. Chem., vol. 20, pp. 12191–1221 (1977).
Das et al., J. Med. Chem., vol. 23, pp. 578–581 (1980).
Dann et al., Ann., vol. 749, pp. 160–194 (1975).
Ashley et al., J. Chem. Soc., pp. 103–116 (1942).
Ashley et al., J. Chem. Soc., pp. 1668–1671, 3089–3093 (1957).
The Merck Index, 9th Ed., Monograph Nos. 3258, 6912, 6994, 8597 (1976).
Das et al. [A] J. Med. Chem. V. 20, pp. 531–536 (1977).
Dann et al. [A] Ann. V. 749, pp. 68–89 (1971).
Berg, J. Chem. Soc. pp. 5097–5101 (1961).
Anné et al., Antimicrobial Agents and Chemotherapy, V. 18, pp. 231–239 (1980).
Clercq et al., J. Med. Chem. V. 23, pp. 787–795 (1980).
Steck et al., Experimental Parasitology, V. 52, pp. 404–413 (1981).

Primary Examiner—Richard A. Schwartz
Assistant Examiner—Kurt G. Briscoe
Attorney, Agent, or Firm—Charles J. Knuth; Albert E. Frost; Robert K. Blackwood

[57] ABSTRACT

Diamidines of the formula

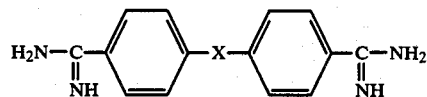

wherein X is a propylene, isobutylene, guanidine, pyrrole, tetrazole, imidazole or substituted imidazole group; and 2-[4-(2-imidazolinyl)phenyl]-6-(2-imidazolinyl)indole, are useful in the treatment of certain protozoal infections in mammals, particularly in cattle.

6 Claims, No Drawings

ANTIPROTOZOAL 1,4-DI(P-AMIDINOPHENYL)IMIDAZOLES

This is a division of application Ser. No. 484,803, filed on Apr. 14, 1983, now U.S. Pat. No. 4,546,113.

BACKGROUND OF THE INVENTION

The present invention is concerned with certain diamidines and a bis-imidazoline having antiprotozoal activity, and their use in the control of trypanosomiasis and/or babesiosis in mammals, particularly in cattle.

Trypanosomiasis is a disease of man and animals caused by flagellate blood borne protozoan parasites. The disease is encountered mainly in Africa, where it is transmitted by the Tse Tse fly. Animal typanosomiasis caused by *Trypanosoma congolense* and *T. vivax*, is considered to be the limiting factor for livestock production in most of the African Continent. Although trypanosomiasis can be fatal to man, its devastating effect on meat producing animals has indirectly caused much more human suffering due to protein starvation. Babesiosis is another hemo-protozoan disease of livestock and is economically important in the tropical and subtropical regions of the world.

Previously reported diamidines having antiprotozoal activity include

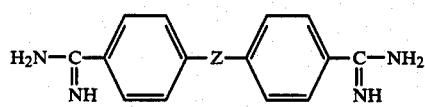
(I)

wherein Z is:
- —NH—N=N— (diminazene, see The Merck Index, 9th Ed., monograph No. 3258);
- —CH=CH— (stilbamidine, loc. cit., monograph No. 8597; Ashley et al. [A], J. Chem. Soc., pp. 103-116, 1942);
- —CH=CH—CH=CH— (Ashley et al. [A]).
- —O(CH$_2$)$_p$O—, where p=1 to 10 (Ashley et al. [A]; when p=5, pentamidine, loc. cit., monograph No. 6912); or
- —O— (phenamidine, loc. cit., monograph No. 6994); and

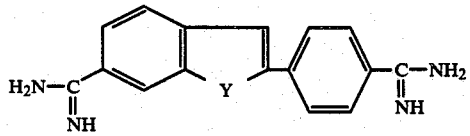
(II)

wherein Y is O, S, NH, NCH$_3$ or CH$_2$ (Dann et al. [A], Ann. vol. 749, pp. 68-89, 1971; Dann, U.S. Pat. Nos. 3,652,591 and 3,689,506).

On the other hand, compounds failing to protect (cure) mice against a protozoal infection include those compounds of the formula (I) wherein Z is —CO—, —CHOH—, —CH$_2$CO—, —CH=CHCO—, —NHCO—, —SO$_2$—, —NHSO$_2$—, —S—S—, —N=N—, —NHNH—, —N=N(O)—, —CH$_2$—, —S—, —CH$_2$NH—, —NHCONH—, —OCH$_2$OCH$_2$O—, —CH$_2$SCH$_2$—, —CH$_2$NHCH$_2$—, —OCH$_2$(p—C$_6$H$_4$)CH$_2$O— or —CH$_2$O(p—C$_6$H$_4$)OCH$_2$—; in spite of the fact that the compounds having the last seven values of Z did show an early and favorable effect on the level of trypanosomes in the peripheral blood stream (Ashley et al. [A]; Ashley et al. [B], J. Chem. Soc., pp. 3089-3093, 1957). Furthermore, replacement of —O(CH$_2$)$_4$O— in (I) with an olefinic variant, —OCH$_2$CH=CHCH$_2$O—, leads to considerable less activity against *T. rhodesiense* and inactivity against *T. congolense* (Ashley et al. [C], J. Chem. Soc., pp. 1668-1671, 1957); substitution of the bridging group in diminazene with a methyl group, i.e., Z+—N(CH$_3$)N=N—, reduces activity by about 75% (Ashley et al. [B]); and the m, m'-isomers of the compounds (I) wherein Z is —O(CH$_2$)$_3$O— or —O(CH$_2$)$_5$O— are about half as active as the p, p'-isomers.

Among the diamidines reported to have antiprotozoal activity are a number of compounds having the formula (I) wherein Z is represented by one of the following 5-membered heterocyclic groups:

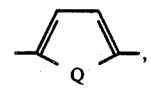

where Q is O, S, NH or N(CH$_3$);

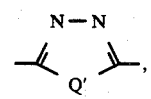

where Q' is S, NH or CH$_2$;

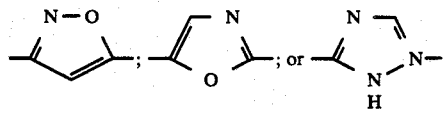

(Das et al. [A], J. Med. Chem. Vol. 20, pp. 531-536, 1977; Das et al. [B], ibid., Vol. 20, pp. 1219-1221, 1977; Das et al. [C], ibid., Vol. 23, pp. 578-581, 1980; Dann et al. [B], Ann. pp. 160-194, 1975). For a similar compound (I), wherein Z is

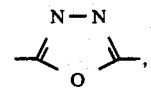

reports concerning activity are conflicting. Thus, against *T. rhodesiense* infections in mice, Das et al. [C] reports no more than a minor increase in mean survival time, at a dose of 40 mg/kg; while earlier Dann et al. [B]reported minimum curative dose of 1-10 mg/kg for the same compound against the same microorganism.

It has also been previously noted by Berg (J. Chem. Soc., pp. 5097-5101, 1961) that the compound of the formula (I) wherein Z is —NHCONH— is lacking in activity, although the corresponding meta isomer:

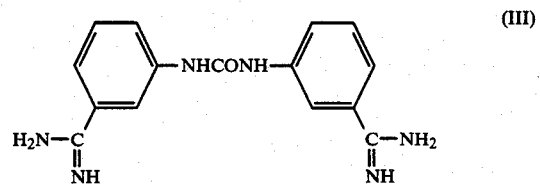
(III)

showed considerable activity. Berg further noted that replacement of the —NHCONH— group in (III) with —NHC(=NH)NH—, —NHC(=NCH₃)NH— or —NHCSNH— led to lowered activity.

The bis-imidazoline compound of the formula

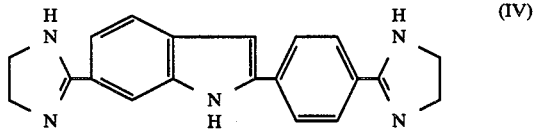
(IV)

presently discovered to have antiprotozoal activity, has been previously reported to have antifungal activity (Anne et al., Antimicrobial Agents and Chemotherapy, vol. 18, pp. 231–239, 1980), and to inhibit oncornaviral DNA polymerase (De Clercq et al., J. Med. Chem., Vol. 23, pp. 787–795, 1980). Neither Anne et al. nor DeClercq et al. describe compound (IV) per se, nor do they provide a method of preparation therefor. For this reason, a detailed preparation method for this compound is included below.

SUMMARY OF THE INVENTION

The present invention encompasses compounds of the formula

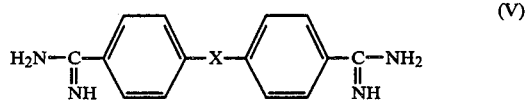
(V)

wherein X is —CH₂CH=CH—, —CH₂C(CH₃)=CH—, —NHC(=NH)NH—,

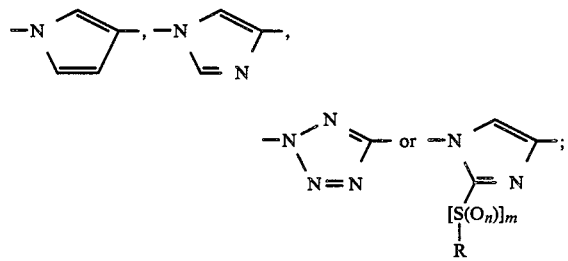

n is 0, 1 or 2;
m is 0 or 1;
R is (C₁–C₃)alkyl, 2-hydroxyethyl, 2,3-dihydroxypropyl, benzyl or 2-, 3- or 4-picolyl; with the provisos that when R is 4-picolyl, m is 1; and when R is methyl and m is 1, n is other than O;
and the pharmaceutically-acceptable acid addition salts thereof. Such salts include, but are not limited to, those formed with HCl, H₂SO₄, H₃PO₄, propionic acid, succinic acid, maleic acid, citric acid, methanesulfonic acid, isethionic acid, p-toluenesulfonic acid and aceturic acid. The preferred salts, because of their more consistent biological activity, are those with HCl.

It is clear from the above background of the invention that the present art is highly unpredictable in character. Present studies have further proven that view to be correct, in that we are now able to extensively add to the list of compounds of the formula (I) which are lacking in antiprotozoal activity. For example, those compounds wherein Z is —C(CH₃)=CHCH₂—, —CH=C(C₆H₅)CH₂—, —CH=C(CO₂CH₃)CH₂—, —N=C(NHCH₃)NH— or

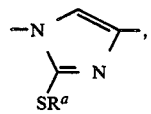

where $R^a$ is —CH₂CH=CH₂ or CH₃, when tested in mice against *T. congolense* or *B. rodhaini* by the method detailed below, show no activity against either microorganism at a dose of 50 mg/kg. In spite of these facts, it has now been discovered that the compounds of the formula (V) possess valuable antiprotozoal activity, in particular, in vivo activity against *Trypanosome congolense* and/or *Babesia rodhaini*, as determined in laboratory induced infections in mice, reflecting general utility in the treatment of trypanosomiasis and/or babesiosis in mammals, particularly in cattle. The activity of the present p-substituted compounds is particularly surprising in view of the teaching of Berg (cited above) and the further fact that m-isomers of the present compounds show no useful activity against either of the above microorganisms (vide post).

The present invention also encompasses a pharmaceutical composition for use in the treatment of a susceptible protozoan infection in a mammal, comprising an antiprotozoal compound of the formula (V) and a pharmaceutically inert carrier; and a method of treating an infection in a mammal caused by a susceptible protozoan, which comprises administering an antiprotozoal amount of a compound of the formula (V).

The present invention further encompasses that same treatment method, but with the compound of the formula (IV), above, or a pharmaceutically-acceptable salt thereof; and a sterile pharmaceutical composition suitable for parenteral administration to a mammal which is infected with a susceptible protozoan, said composition comprising an antiprotozoal effective amount of a compound of the formula (IV), at a concentration of at least 1% (w/v), and a pharmaceutically inert carrier.

DETAILED DESCRIPTION OF THE INVENTION

The bis-amidine compounds (V) of the present invention are readily prepared from a corresponding dinitrile of the formula

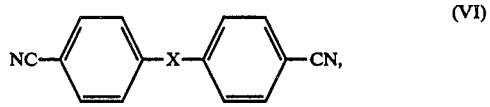
(VI)

wherein X is as defined above; via an intermediate dicarboximidate ester of the formula

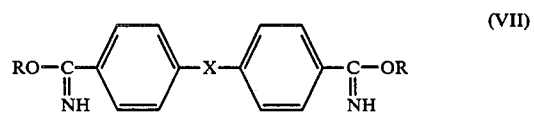
(VII)

wherein X is as defined above and R is (C₁–C₅)alkyl or (C₂–C₅)alkoxyalkyl. Preferred values of R are methyl, ethyl and 2-methoxyethyl.

The first stage, (VI)→(VII), is carried out by reacting the dinitrile (VI) with at least 2 equivalents of an alcohol (ROH, where R is as defined above) in the presence of at least 2 equivalents of a strong, anhydrous acid (e.g., HCl, H$_2$SO$_4$ or sulfonic acid such as methanesulfonic acid, isethionic acid or p-toluenesulfonic acid), under anhydrous conditions in a reaction-inert solvent, conveniently in an excess of the alcohol, ROH, optionally diluted with a further reaction-inert solvent such as chloroform. Preferred alcohols (methanol, ethanol, 2-methoxyethanol) correspond to the preferred groups R, as specified above. Temperature is not critical, the range −20° to 50° C. being fully satisfactory. Ambient temperature is preferred, avoiding costs associated with cooling or heating. The preferred acid is dry HCl conveniently introduced in excess by perfusing the alcoholic solvent at −20° to 0° C. prior to reaction with the dinitrile. The intermediate dicarboximidate ester (VII) is readily isolated from the reaction mixture, usually in the form of an addition salt with the acid used in the process. Said isolation is accomplished by standard methods of concentration, and/or addition of a non-solvent or of a further excess of the acid, as necessary to obtain a recoverable solid.

As used herein, the expression "reaction-inert solvent" refers to any solvent which does not react with reactants, intermediates or product in a manner which adversely affects the yield of the desired product.

The second stage, (VII)→(V), is carried out by reacting the dicarboximidate ester (VII), usually in the form of an acid addition salt, with excess ammonia (at least four equivalents, to form the bis-amidine, plus at least one equivalent for each equivalent of acid associated with the addition salt). Temperature is not critical; again, the range 0°-50° C. being fully satisfactory, with ambient temperatures preferred. The reaction is usually carried out in anhydrous reaction-inert solvent, alcohols such as those used in the above first stage being particularly well-suited. In this case, it will be noted that the alcohol need not correspond to the value of R in the starting material, since even although a different alcohol may interact with the starting material (by ester exchange), there will be no adverse effect on yield. The diamidine product (V) is isolated, most conveniently in the form of the same acid addition salt as that introduced into the present stage, by the same standard methods detailed above for the isolation of intermediate ester (VII). If an alternative salt of (V) is desired, it is preferable to first convert the isolated salt to the free base form, a conversion which is conveniently done by neutralization of the acid addition salt in water, with recovery of free base by filtration or extraction into a water immiscible solvent. The free base is then contacted with the appropriate acid in a reaction-inert solvent. Those salts which do not precipitate directly are isolated by concentration and/or by addition of a non-solvent.

When the final product contains an optional sulfone or sulfoxide group and that group is not already present in the starting dinitrile, it can be introduced by the oxidation of a corresponding thioether derivative. An oxidizing agent particularly well-suited to the present purpose is 30% H$_2$O$_2$, with substantially 1 equivalent used to form the sulfoxide and at least 2 equivalents used to form the sulfone. Either oxidation is generally carried out in the presence of a reaction-inert solvent (e.g., methanol). Temperature is not critical, the range 0°-50° C. being fully satisfactory; ambient temperatures are preferred.

The dinitriles (VI) required as starting materials for synthesis of the present diamidine compounds are readily prepared from known compounds (available commercially or prepared according to literature methods). Preparations 1-50 detailed below provide extensive exemplification of methods for the preparation of said dinitriles.

The utility of the compounds (IV) and (V) in the treatment of trypanosomiasis and/or babesiosis is demonstrated by their in vivo activity against *Trypanosome congolense* and *Babesia rodhaini* infections in mice. Groups of mice (usually 10 in number) are infected, usually intraperitoneally, with a multiple of the 100% lethal dose of the microorganism. The ability of a given subcutaneous dose of the test compound to prevent death over a 4 week period is then determined. Activity is expressed as % protection, i.e., the proportion of the group of lethally infected mice which survive at the given dosage. Because they show at least 80% protection at a subcutaneous dose of 50 mg/kg, against both *Trypanosome congolense* and *Babesia rodhaini*, most highly preferred compounds of the formula (V) are those wherein X is —CH$_2$CH=CH$_2$,

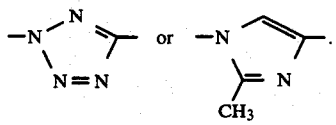

Additional preferred compounds, because they show at least 90% protection against *Trypanosome congolense* at a dose no higher than 50 mg/kg, are the three compounds of the formula (V) wherein X is —NHC(=NH)NH—, or

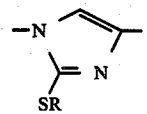

with R as 4-picolyl; although it is further noted that these two compounds, (like the compound wherein X is

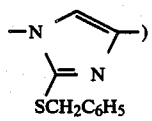

show 0% protection against *Babesia rodhaini*. Further preferred compounds, because they show at least 90% protection against *Babesia rodhaini* at a dose no higher than 50 mg/kg, are the four compounds of the formula (V) wherein X is —CH$_2$C(CH$_3$)=CH—,

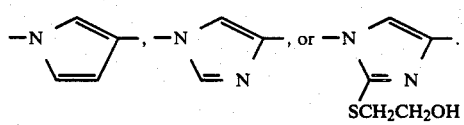

Of the latter compounds, the third is more preferred, also showing 40% protection against *Trypanosome congolense* at 50 mg/kg. It is further noted that the first of these four compounds shows 10% protection against *Trypanosome congolense* at 50 mg/kg, while the second and fourth (like compounds of the formula (V) wherein X is

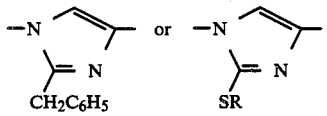

where R is 2-picolyl or 3 picolyl) show 0% protection against *Trypanosome congolense* at 50 mg/kg. The compound of the formula (IV) is also a preferred compound, in that it shows 100% protection against *Babesia rodhaini* at a dose of 6.25 mg/kg (although it shows 0% protection against *Trypanosome congolense* even at 100 mg/kg.)

By way of contrast, known 1,3-di(m-amidinophenyl)-guanidine of Berg (cited above) showed no activity against *Trypanosome congolense* or *Babesia rodhaini* (at 50 mg/kg or 25 mg/kg, respectively); and the further m-disubstituted amidine, 1,3-di(m-amidinophenyl)propene (isomeric with one of the present most highly preferred compounds) showed no activity against *Trypanosome congolense* at 50 mg/kg, and although showing 33% protection against *Babesia rodhaini* at 25 mg/kg, was toxic at this dose.

In treating natural infections in mammals due to a susceptible protozoan, the mammal is dosed, preferable parenterally (e.g., subcutaneously, intramuscularly or intraperitoneally) with 1–100 mg of the active compound (in single or divided doses) per kilogram of body weight of the mammal.

The compounds of the formulae (IV) and (V) are formulated in sterile form for parenteral administration (injection) according to methods well known in the pharmaceutical art, employing such standard excipients, buffers, solvents, suspending agents and preservatives as are commonly employed for such parenteral dosage forms. These formulations can be solutions or suspensions; in preconstituted liquid form, or as dry powders for reconstitution shortly before injection. The concentration of drug in vehicle will generally be relatively high (e.g., 5-20%), certainly at least 1% w/v, in order to minimize the volume of injection.

The present invention is illustrated by the following examples. However, it should be understood that the invention is not limited to the specific details of these examples. Unless otherwise specified, all operations were carried out at ambient temperature; all temperatures are in degrees centigrade; stripping of all solvents was carried out at reduced pressure; all tlc (thin layer chromatography) was carried out on commercial silica gel plates containing an ultra violet sensitive detector, with the eluant specified in parentheses; all solution drying was over $MgSO_4$; and all solvent ratios are by volume. The abbreviations DMF, THF and DMSO refer, respectively, to dimethylformamide, tetrahydrofuran and dimethylsulfoxide.

EXAMPLE 1

Diethyl p,p'-(1,3-Diphenylpropene)dicarboximidate Dihydrochloride 1,3-Di(p-cyanophenyl)propene (11.9 g, 0.049 mole) was taken into 640 ml 15:1 $CHCl_3$: absolute ethanol, cooled to $-10°$ to $0°$ and perfused with HCl gas for 65 minutes, then allowed to stand at room temperature for 40 hours and finally stripped to yield title product as a white solid; 15.5 g; ir(KBr) 3.45, 6.25, 6.90, 7.25, 7.35 and 9.25 microns.

EXAMPLE 2

1,3-Di(p-amidinophenyl)propene Dihydrochloride

Absolute ethanol (350 ml) was saturated with $NH_3$ at $0°-5°$ by perfusing with NH gas for 25 minutes. Title product of the preceding Example (15.5 g, 0.038 mole) was added, the mixture was allowed to warm to room temperature and stirred for 4 days. Crystallization was induced by cooling to $0°-5°$ C. for 2 hours. After granulating for 1 day at room temperature, title product was recovered by filtration with acetone wash: 7.2 g; m.p. 314°–318° ; tlc (2:1:1 butanol:$H_2O$:$CH_3CO_2H$) Rf 0.34.

Analysis: Calculated: C, 55.34; H, 6.02; N, 15.18; Cl$^-$, 19.21. Found: C, 55.10; H, 5.98; N, 15.21; Cl$^-$, 19.06.

To obtain a second crop, the filtrate was stripped to a yellow foam which was triturated with acetone, stirred with 50 ml 2N HCl (initially added dropwise) and filtered with acetone wash: 3.3 g; m.p. 314°–318°.

EXAMPLE 3

Diethyl p,p'-(2-Methyl-1,3-diphenylpropene)dicarboximidate Dihydrochloride 1,3-Di(p-cyanophenyl)-2-methylpropene (800 mg) was converted to title product by the method of Example 1. After stripping, the resulting foam was triturated with acetone: 1.2 g; ir(KBr) 3.0, 3.40, 6.25, 6.95, 7.25, 7.45 and 9.45 microns.

EXAMPLE 4

2-Methyl-1,3-di(p-amidinophenyl)propene Dihydrochloride

Title product of the preceding Example (1.2 g) was converted to present title product by the method of Example 2. After 4 days at room temperature, the reaction mixture was stripped to yield title product as an oil which solidified on trituration with acetone: 766 mg; tlc (2:1:1 butanol:$H_2O$:$CH_3CO_2H$) Rf 0.6; ir(KBr) 3.05, 3.25, 6.06, 6.25, 6.50 and 6.75 microns.

EXAMPLE 5

Di(2-methoxyethyl) p,p'-(1,3-Diphenylguanidine)dicarboximidate Dihydrochloride

2-Methoxyethanol (35 ml) was cooled in an acetoneice bath and purged with dry HCl for 20 minutes. 1,3-Di(p-cyanophenyl)guanidine (500 mg) was added and the mixture warmed to room temperature and stirred 20 hours. The reaction mixture was stripped of excess HCl, poured into 300 ml ether, granulated and title product recovered by filtration; ir(KBr) 2.92, 3.48, 6.00, 6.21, 6.95, 8.00, 8.32, 8.80 and 9.10 microns. The entire product was used in the next step.

EXAMPLE 6

1,3-Di(p-amidinophenyl)guanidine Dihydrochloride

The entire title product from the preceding Example was taken into absolute ethanol (50 ml), cooled to 0°-5° C., and the solution purged with NH$_3$ for 15 minutes. After stirring for 60 hours at room temperature, the reaction mixture was stripped to solids, which were slurried in 5 ml methanol and cooled to 0°-5° C. The cold slurry was purged with dry HCl, initially forming a solution from which title product crystallized: 595 mg; m.p. 325°-330°; ms 261, 244, 236; high resolution ms 278, 261, 244 (no oxygen); tlc (2:1:1 butanol:H$_2$O:CH$_3$CO$_2$H) Rf 0.05.

EXAMPLE 7

Di(2-methoxyethyl) p,p'-(1,3-Diphenylpyrrole)dicarboximidate Dihydrochloride By the method of Example 5, 1,3-di(p-cyanophenyl)-pyrrole (600 mg) was converted to present title product: 974 mg; ir(KBr) 3.00, 3.45, 5.90, 6.25, 6.90, 7.40, 7.85, 8.35 and 9.45.

EXAMPLE 8

1,3-Di(p-amidinophenyl)pyrrole Dihydrochloride

Title product of the preceding Example (974 mg) was converted to present title product by the method of Example 2, it being unnecessary to cool the reaction mixture to induce precipitation of the product. At the end of the reaction period, the reaction mixture was filtrated and the filtrate reserved. The filter cake was repulped for 10 minutes in 8 ml 2N HCl and refiltered with acetone wash to yield a first crop of title product: 200 mg; ms 303, 286, 269; ir(KBr) shows amidine band at 6.00 microns; tlc (2:1:1 butanol:H$_2$O:CH$_3$CO$_2$H) Rf 0.27.

Analysis: Calculated: C, 54.84; H, 5.38; N, 17.76; Cl$^-$17.98 Found: C, 55.24; H, 5.62; N, 17.44; Cl$^-$16.71.

A second crop was obtained by stripping the reserved filtrate to solids which were then further processed as above: 160 mg.

EXAMPLE 9

Di(2-methoxyethyl) p,p'-(1,4-Diphenylimidazole)dicarboximidate Dihydrochloride By the method of Example 5, 1,4-di(p-cyanophenyl)imidazole (436 mg) was converted to present title product: 721 mg; ir(KBr) 3.00, 3.50, 6.10-6.25, 6.90, 7.15, 7.85, 8.70, 8.85, 9.20 and 9.35 microns.

EXAMPLE 10

1,4-Di(p-amidinophenyl)imidazole Dihydrochloride

By the method of Example 8, title product of the preceding Example (721 mg) was converted to present title product. The crude product which was isolated directly from the reaction mixture (330 mg) was slurried in 30 ml ethanol, purged with dry HCl, cooled and refiltered to yield purified title product: 239 mg; m.p. 359°-361° (dec.); tlc (2:1:1 butanol:H$_2$O:CH$_3$CO$_2$H) Rf 0.26.

A second crop (75 mg) was obtained by concentration of the ethanol mother liquor.

EXAMPLE 11

Di(2-methoxyethyl) p,p'-(2,5-Diphenyltetrazole)dicarboximidate Dihydrochloride By the method of Example 5, 2,5-di(p-cyanophenyl)-tetrazole (400 mg) was converted to present title product: 666 mg (91%); ir(KBr) 2.90, 3.45, 6.10, 6.85, 7.15, 7.90, 8.50, 8.90, 9.30 and 9.85 (doublet) microns.

EXAMPLE 12

2,5-Di(p-amidinophenyl)tetrazole Dihydrochloride

By the method of Example 8, title product of the preceding Example (660 mg) was converted to present title product. The crude product isolated directly from the reaction mixture was repulped sequentially in ethyl acetate, 2N HCl and acetone to yield purified title product: 284 mg; tlc (2:1:1 butanol:H$_2$O:CH$_3$CO$_2$H) Rf 0.14; ms 261, 244, 116.

EXAMPLE 13

Di(2-methoxyethyl) p,p'-(1,4-Diphenyl-2-methylimidazole)dicarboximidate Dihydrochloride By the method of Example 5, 1,4-di(p-cyanophenyl)-2-methylimidazole (350 mg, 0.0012 mole) was converted to present title product: 611 mg; ir(KBr) 2.82, 3.42, 6.10, 6.20, 6.95, 7.38 and 9.00 microns.

EXAMPLE 14

1,4-Di(p-amidinophenyl)-2-methylimidazole Dihydrochloride

By the method of Example 4, title product of the preceding Example (611 mg) was converted to present title product. The reaction mixture, which was clarified prior to stripping, gave crude product as a yellow foam. The latter was triturated with acetone and then a combination of acetone and 2N HCl, and finally filtered with acetone wash to yield title product: 378 mg; pnmr/DMSO-d$_6$/delta 2.85 (s, 3H, CH$_3$), 8.0-8.65 (m, 9H, aromatic), 9.45-10.1 (bd. t, 8H, protonated amidine groups)ppm.

EXAMPLE 15

Di(2-methoxyethyl) p,p'-(1,4-diphenyl-2-benzylimidazole)dicarboximidate Dihydrochloride By the method of Example 5, 1,4-di(p-cyanophenyl)-2-benzylimidazole (240 mg) was converted to present title product: 370 mg; ir(KBr) 2.94, 3.40, 6.05, 6.15 and 7.35 microns.

EXAMPLE 16

1,4-Di(p-amidinophenyl)-2-benzylimidazole Dihydrochloride

By the method of Example 14, title product of the preceding Example (370 mg) was converted to present title product: 225 mg; ir(KBr) no CN band, C≡N band at 6.00 microns; tlc (2:1:1 butanol:H$_2$O:CH$_3$CO$_2$H) Rf 0.39. Title product (195 mg) was further purified by dissolving in 15 ml methanol, briefly purging with dry HCl, stripping, triturating with cold 2N HCl, and filtering with 2N HCl and finally acetone wash: 116 mg.

EXAMPLE 17

Di(2-methoxyethyl)
p,p'[1,4-Diphenyl-2-(2-picolyl)imidazole]dicarboximidate Trihydrochloride By the method of Example 5, 1,4-di (p-cyanophenyl)-2-(2-picolyl)imidazole hydrochloride (580 mg) was converted to present title product: 930 mg; ir(KBr) 2.90, 3.44, 6.20, 6.85, 7.15, 7.35 and 8.32 microns.

EXAMPLE 18

1,4-Di(p-amidinophenyl)-2-(2-picolyl)imidazole Trihydrochloride

By the procedure of Example 4, title product of the preceding Example (925 mg) was converted to present title product. The initially isolated, crude oil was combined with acetone, diluted dropwise with 2N HCl and then with methanol. Since oily material remained, the whole was restripped, the residue was treated with 5 ml $CH_3OH$, and solids (160 mg) recovered by filtration. The filtrate was purged with HCl gas for 2 minutes and then diluted with 50 ml acetone to precipitate title product, which was recovered by filtration with acetone wash: 393 mg; m.p. 215° (dec.); ir(KBr) no CN band, includes C=N band at 6.00 microns; tlc (2:1:1 butanol:-$H_2O:CH_3CO_2H$) Rf 0.10.

EXAMPLE 19

Di(2-methoxyethyl)
p,p'(1,4-Diphenyl-2-methylthioimidazole)dicarboximidate Dihydrochloride By the method of Example 5, 1,4-di(p-cyanophenyl)-2-methylthioimidazole (340 mg) was converted to present title product: 456 mg; ir(KBr) 2.91, 3.44, 6.20, 6.85, 7.15, 7.35 and 8.32 microns.

EXAMPLE 20

1,4-Di(p-amidinophenyl)-2-methylthioimidazole Dihydrochloride

By the procedure of Example 4, title product of the preceding Example (456 mg) was converted to present title product. Following trituration with acetone, the product was further triturated with a mixture of acetone and 2N HCl and recovered by filtration with acetone wash: 248 mg; pnmr($CDCl_3$) includes singlet at 2.7 ppm ($SCH_3$); ir(KBr) no CN band, includes C=N band at 6.00 microns; ms includes 333 (m-17) and 316 (m-34); tlc (2:1:1 butanol:$H_2O:CH_3CO_2H$) Rf 0.25.

EXAMPLE 21

1,4-Di(p-amidinophenyl)-2-methanesulfonylimidazole Dihydrochloride

Title product of the preceding Example (225 mg) was dissolved in 10 ml $CH_3OH$ and cooled to 0°–5° C. Excess 30% $H_2O_2$ (50 drops, greater than 2 equivalents) was added and the mixture warmed to room temperature, stirred 60 hours, and finally stripped to an oil which was solidified by trituration with methanol to yield title product: 221 mg; tlc (2:1:1 butanol:$H_2O:CH_3CO_2H$)Rf 0.15.

By restricting the amount of $H_2O_2$ to 1 equivalent, the corresponding sulfoxide, 1,4-di(p-amidinophenyl)-2-methanesulfinylimidazole dihydrochloride, is obtained.

EXAMPLE 22

Di(2-methoxyethyl)
p,p'-(1,4-Diphenyl-2-propylthioimidazole)dicarboximidate Dihydrochloride By the method of Example 5, 1,4-di(p-cyanophenyl)-2-propylthioimidazole (500 mg) was converted to present title product; ir(KBr) 2.95, 3.40, 6.20, 6.80, 7.30, 8.80 and 9.10 microns. The entire batch of product was used in the next step.

EXAMPLE 23

1,4-Di(p-amidinophenyl-2-propylthioimidazole Dihydrochloride

By the method of Example 4, title product of the preceding Example (entire batch) was converted to present title product. Prior to stripping, the reaction mixture was treated with activated carbon. The crude residue, after stripping, was taken up in 5 ml $CH_3OH$, the solution purged for 10 minutes with dry HCl, and title product precipitated by dilution with acetone: 381 mg; ms 362, 345, 302, 232, 219; tlc (2:1:1 butanol:-$H_2O:CH_3CO_2H$) Rf 0.50.

EXAMPLE 24

Di(2-methoxyethyl)
p,p'-[1,4-Diphenyl-2-(2-hydroxyethylthio)imidazole]-dicarboximidate Dihydrochloride By the method of Example 5, 1,4-di(p-cyanophenyl)-2-(2-hydroxyethylthio)imidazole (500 mg) was converted to present title product: 817 mg; ir(KBr) 2.90, 3.40, 6.25, 6.95 and 9.35.

EXAMPLE 25

1,4-Di(p-amidinophenyl)-2-(2-hydroxyethylthio)-imidazole Dihydrochloride

By the method of Example 6, title product of the preceding Example (817 mg) was converted to present title product, which was precipitated from the methanol/HCl by dilution with acetone: 377 mg; m.p. >250°; tlc (2:1:1 butanol:$H_2O:CH_3CO_2H$) Rf 0.42.

EXAMPLE 26

Di(2-methoxyethyl)
p,p'-[1,4-Diphenyl-2-(2,3-dihydroxypropylthio)imidazole]dicarboximidate Dihydrochloride By the method of Example 5, 1,4-di(p-cyanophenyl)-2-(2,3-dihydroxypropylthio)imidazole (331 mg) was converted to present title product; ir(KBr) 2.90, 3.40, 6.25, 6.85, 7.35 and 9.00. The entire batch was used in the next step.

EXAMPLE 27

1,4-Di(p-amidinophenyl)-2-(2,3-dihydroxypropylthio)imidazole Trihydrochloride

By the procedure of Example 6, title product of the preceding Example (the entire batch) was converted to present title product: 296 mg; ms 267, 252, 209; tlc (2:1:1 butanol:$H_2O:CH_3CO_2H$) Rf 0.25.

EXAMPLE 28

Di(2-methoxyethyl) p,p'-[1,4-Diphenyl-2-(3-picolylthio)imidazole]dicarboximidate Trihydrochloride By the procedure of Example 5, 1,4-Di(p-cyanophenyl)-2-(3-picolylthio)imidazole (0.48 g) was converted to present title product: 0.78 g, ir(KBr) 2.90, 3.40, 6.25, 6.95, 7.45 and 9.10.

EXAMPLE 29

1,4-Di(p-amidinophenyl)-2-(3-picolylthio)imidazole Trihydrochloride

By the method of Example 4, title product of the preceding Example (0.78 g) was converted to present title product. The initially formed oil was taken up in 2 ml of 2N HCl and crystallized by slowly adding 10 ml of acetone to the stirred solution: 0.37 g; ms 393 (m-2NH$_3$); ir(KBr) no CN band, C=N band at 6.00 microns; tlc (2:1:1 butanol:H$_2$O:CH$_3$CO$_2$H) Rf 0.14.

EXAMPLE 30

Di-(2-methoxyethyl) p,p'[1,4-Diphenyl-2-(4-picolylthio)imidazole]dicarboximidate Trihydrochloride By the method of Example 5, 1,4-di(p-cyanophenyl)-2-(4-picolylthio)imidazole (500 mg) was converted to present title product, ir(KBr) 2.95, 3.40, 6.30, 6.70, 6.95 and 7.90 microns. The entire batch of product was used in the next step.

EXAMPLE 31

1,4-Di(p-amidinophenyl)-2-(4-picolylthio)imidazole Trihydrochloride

By the method of Example 6, the entire batch of title product from the preceding Example was converted to present title product: 500 mg; m.p. 230°-240°; ms 395, 301, 243; tlc (2:1:1 butanol:H$_2$O:CH$_3$CO$_2$H) Rf 0.08. A second crop (128 mg) was obtained from mother liquor by addition of acetone.

EXAMPLE 32

Di-(2-methoxyethyl p,p'[1,4-Diphenyl-2-(2-picolylthio)imidazole]dicarboximidate Trihydrochloride By the method of Example 5, 1,4-di(p-cyanophenyl)-2-(2-picolylthio)imidazole (500 mg) was converted to present title product; ir(KBr) 2.90, 3.40, 6.30, 6.85, 7.15, 7.35 and 9.20 microns. The entire batch of product was used in the next step.

EXAMPLE 33

1,4-Di(p-amidinophenyl)-2-(2-picolylthio)imidazole Trihydrochloride

By the procedure of Example 25, the entire batch of title product of the preceding Example was converted to present title product: 729 mg; ms 393, 360, 259, 243; tlc (2:1:1 butanol:H$_2$O:CH$_3$CO$_2$H) Rf 0.17.

EXAMPLE 34

Di(2-methoxyethyl) p,p'-(1,4 Diphenyl-2-benzylthioimidazole Dihydrochloride

By the method of Example 5, 1,4 di(p-cyanophenyl)-2-(benzylthio)imidazole was converted to present title product: 300 mg; ir(KBr) 2.90, 3.40, 6.30, 6.85, 7.35 and 7.80 microns.

EXAMPLE 35

1,4-Di(p-amidinophenyl)-2-(benzylthio)imidazole Dihydrochloride

By the method of Example 6, title product of the preceding Example (300 mg) was converted to present title product. Since the initially formed oil did not crystallize from the cold CH$_3$OH-HCl solution, it was restripped and the residue crystallized by trituration with a mixture of 2N HCl and ethyl acetate: 163 mg; tlc (2:1:1 butanol:H$_2$O:CH$_3$CO$_2$H) Rf 0.50.

EXAMPLE 36

2-[4-(2-Imidazolidinyl)phenyl]-6-(2-imidazolidinyl)indole Dihydrochloride 2-(p-Cyanophenyl)-6-cyanoindole (3.83 g) was slurried in 60 ml ethylenediamine, and the mixture sparged with H$_2$S. An exotherm was noted, with a solution resulting. After 8 minutes sparging, product began to precipitate. The mixture was allowed to cool slowly back to room temperature, stirred for an additional 2 hours and poured into 175 ml 6N NaOH. After stirring 15 minutes, crude product was recovered by filtration with a small amount of 6N NaOH and then water wash. Dried product was dissolved in 1 liter CH$_3$OH, treated with activated carbon, filtered and the filtrate acidified by sparging with excess dry HCl over a 3 minute period, precipitating title product. After granulating 10 minutes, title product was recovered by filtration with methanol and then acetone wash: 5.11 g; m.p. greater than 360°; tlc (2:1:1 butanol:H$_2$O:CH$_3$CO$_2$H) Rf 0.06; ms 329, 300, 233.

Analysis: Calculated for C$_{20}$H$_{19}$N$_5$.2HCl.2H$_2$O C, 54.79; H, 5.70; N, 15.98; Cl$^-$, 16.21. Found: C, 54.98; H, 5.74; N, 16.11; Cl$^-$, 15.93.

PREPARATION 1

Methyl p-Cyanobenzoylacetate

Dimethyl carbonate (126 g, 1.4 moles) was added dropwise to a slurry of NaH (50% in mineral oil, 13.44 g, 0.28 mole) slurried in 280 ml of dry dioxane. The reaction mixture was warmed to 80°-85° and p-cyanoacetophenone (40.7 g, 0.28 mole) in 140 ml dioxane added dropwise (at about ⅔ addition, mechanical loss due to foaming occurred; such losses are avoided by slower addition, e.g., over 1 hour). After addition was complete, heating at 80° was continued for 2 hours and crude product recovered by hot filtration. The cake was distributed between dilute CH$_3$CO$_2$H and ether. The ether layer was separated; washed in sequence with H$_2$O, saturated NaHCO$_3$, H$_2$O and brine; dried; and stripped to yield title product: 39 g, (68.6%); m.p. 93°-98°; tlc (4:1 toluene:ethyl acetate) Rf 0.58. Recrystallization of 0.5 g from 2-propanol gave 0.403 g; m.p. 96°-99°.

PREPARATION 2

Methyl 3-(p-Cyanophenyl)-2-(p-cyanobenzoyl)propionate

Methyl p-cyanobenzoylacetate (17.77 g, 0.087 mole) and p-cyanobenzyl bromide (17.16 g, 0.087 mole) were combined in 525 ml DMF under N$_2$. K$_2$CO$_3$ (12.1 g, 0.087 mole) was added, the slurry stirred 1.5 hours and finally poured into a mixture of 2.5 liters H$_2$O and 0.5 liter ethyl acetate. The organic layer was separated, washed with fresh H$_2$O and then brine, stripped to dryness, and the residue slurried in ether to yield title product: 14.83 g (53.6%); m.p. 154°–157° ; tlc (4:1 toluene:ethyl acetate) Rf 0.44.

PREPARATION 3

1,3-Di(p-cyanophenyl)-1-propanone

Title product of the preceding Preparation (5.80 g, 0.018 mole) was refluxed under N$_2$ in 140 ml 1:1 concentrated HCl:THF for 1.25 hours. The reaction mixture was cooled and title product recovered by filtration: 3.35–3.54 g (71–75%); m.p. 149°–152° C.; tlc (4:1 toluene:ethyl acetate) Rf 0.47.

PREPARATION 4

1,3-Di(p-cyanophenyl)-1-propanol

Title product of the preceding preparation (1.04 g, 0.004 mole) was slurried in 200 ml anhydrous C$_2$H$_5$OH. NaBH$_4$ (0.155 g, 0.004 mole) was added. After 5 minutes, a solution resulted. After 30 minutes, the reaction mixture was stripped to an oil, taken up in ethyl acetate, washed with H$_2$O and then brine, dried and stripped to yield title product: 1.03 g; m.p. 110°–112°.

PREPARATION 5

1,3-Di(p-cyanophenyl)propene

Using a Dean-Stark trap, title product of the preceding Preparation (262 mg, 1 mmole), p-toluenesulfonic acid (270 mg, 1.42 mmole) and 25 ml toluene were combined and refluxed for 3 hours. The reaction mixture was stripped to low volume; diluted with ethyl acetate; washed in sequence with 5% KOH, H$_2$O and brine; dried; and stripped to yield 260 mg of crude product. Chromatography on silica gel with toluene as eluant, collecting the less polar component, gave purified title product: 150 mg; m.p. 98°–105°.

PREPARATION 6

1,3-Di(p-cyanophenyl)acetone

To dry N-methylpyrrolidone was added Na$_2$Fe(CO)$_4$ (25 g, 0.065 mole) and then p-cyanobenzyl bromide (12.7 g, 0.065 mole). A mild exotherm was noted. After stirring 1 hour, more of the bromide (19.0 g, 0.097 mole) was added and stirring continued for 21 hours. The reaction mixture was then poured into 1.8 liters of ether, stirred 1 hour and filtered. The filtrate was stripped to 200 ml, added slowly to 700 ml 2N HCl, cooled and crude product recovered by filtration. The partially dried cake (13.3 g) was taken up in 800 ml hot CH$_3$OH and filtered. The filtrate was boiled down to 200 ml, cooled, and purified title product recovered by filtration: 4.64 g; m.p. 149°–150°; tlc (4:1 toluene:ethyl acetate) Rf 0.41.

PREPARATION 7

1,3-Di(p-cyanophenyl)isopropanol

By the method of Preparation 4, title product of the preceding Preparation (5.2 g, 0.02 mole) was converted to present title product: 5.03–5.18 g (95.9–98.7%); m.p. 157°–160°.

PREPARATION 8

1,3-Di(p-cyanophenyl)isopropyl Mesylate

Title product of the preceding Preparation (1.0 g, 0.0038 mole) and methanesulfonyl chloride (0.94 g, 0.0082 mole) were combined in 16 ml pyridine and stirred under N$_2$ for 4 hours. The reaction mixture was then diluted with 150 ml H$_2$O, granulated and filtered (washing with H$_2$O, 2N HCl and finally fresh H$_2$O) to yield title product: 1.19 g (91.7%); m.p. 140°–143°; tlc (4:1 toluene:ethyl acetate) Rf 0.37.

PREPARATION 9

1,3-Di(p-cyanophenyl)propene

Title product of the preceding Preparation (9.0 g), in a small flask, was melted under N$_2$ by immersion in an oil bath at 200° for 5 minutes. The melt was cooled, taken up in ethyl acetate, washed in sequence with saturated NaHCO$_3$, H$_2$O and brine, dried, treated with activated carbon, stripped and chromatographed on silica gel with toluene as eluant to yield title product, 4.4 g; m.p. 99°–107°.

PREPARATION 10

2-Methyl-1,3-di(p-cyanophenyl)-2-propanol

Title product of Preparation 6 (2.6 g, 0.01 mole) in 100 ml THF, cooled to 5°, was reacted with methylmagnesium chloride (5 ml of 2.8N in ether, 0.014 mole). After 1 hour, the reaction mixture was added to saturated NH$_4$Cl and extracted with ethyl acetate. The extract was washed with H$_2$O and then brine, stripped to solids (2.64 g) and triturated with hot toluene to yield title product: 1.48 g; m.p. 147°–148° C.; tlc (4:1 toluene: ethyl acetate) Rf 0.30.

PREPARATION 11

2-Methyl-1,3-di(p-cyanophenyl)propene

By the method of Preparation 5, title product of the preceding Preparation (1.12 g, 0.004 mole) was converted to present title product: 1.24 g crude; 944 mg after chromatography; oil; ms 258, 243, 140; tlc (4:1 toluene:ethyl acetate) Rf 0.7.

PREPARATION 12

1,3-Di(p-cyanophenyl)guanidine

Cyanogen bromide (3.18 g, 0.03 mole) and p-cyanoaniline (7.08 g, 0.06 mole) were combined in 30 ml absolute ethanol and refluxed 16 hours. The reaction mixture was then cooled and diluted with 170 ml ether. The resulting slurry was granulated 0.5 hour, filtered with 2N NaOH wash and the cake dried (6.04 g). The cake was repulped in 300 ml ether, filtered, repulped in ethyl acetate and again filtered. The ether filtrate was stripped and the residue recrystallized from 2-propanol to yield title product: 0.55 g; m.p. 195°–200°; ir(KBr) strong CN signal; ms 261, 144, 118; tlc (ethyl acetate) Rf 0.48. The ethyl acetate filtrate was stripped and the residue chromatographed on silica gel with ethyl acetate as eluant and tlc monitoring, to yield additional title product 1.32 g; m.p. 196°–200° C.; ms 261, 144, 118.

PREPARATION 13

N-(p-Bromophenyl)-p-cyanophenacylamine p-Cyanophenacyl bromide (29.8 g, 0.138 mole) and p-bromoaniline (47.13 g, 0.266 mole) were combined with 53.2 g of absolute ethanol and stirred 16 hours. The solution was then diluted with ether and the resulting slurry filtered. The filter cake was repulped in 500 ml ether, filtered, repulped in 400 ml acetone and again filtered to yield title product: 17.14 g (40.9%); m.p. 154°–157°.

PREPARATION 14

Dimethyl 1-(p-Bromophenyl)-4-(p-cyanophenyl)pyrrole-2,3-dicarboxylate

Title product of the preceding Preparation (9.45 g, 0.030 mole) and dimethyl acetylenedicarboxylate (8.52 g, 0.060 mole) were combined with 30 ml CH$_3$OH, and the slurry refluxed for 4 hours. The reaction mixture was cooled in an ice-water bath. The resulting solids were recovered by filtration and recrystallized from 2-propanol to yield title product: 6.46 g; m.p. 178°–180°.

PREPARATION 15

1-(p-Bromophenyl)-4-(p-cyanophenyl)pyrrole-2,3-dicarboxylic Acid

Title product of the preceding Preparation (7.62 g, 0.0173 mole) and LiI (23.3 g, 0.173 mole) were combined in 150 ml DMF. NaCN (1.70 g, 0.0346 mole) was added portionwise, as the temperature rose to 41° C. The reaction mixture was heated at 120° C. for 16 hours, then cooled and filtered. The filtrate was reserved and the filter cake was taken up in 200 ml of warm H$_2$O. The resulting solution was cooled to room temperature, acidified to pH 1.4 with 2N HCl and title product recovered by filtration: 2.58 g; m.p. 222°–224°; ms 412/410. The reserved filtrate was carefully acidified to pH 1.4 with 2N HCl (trapping HCN wih a 6N NaOH trap) to provide additional title product; 4.03 g; m.p. 217°–221°; ms 412/410; tlc (4:1 toluene:ethyl acetate) Rf 0.0.

PREPARATION 16

1,3-Di(p-cyanophenyl)pyrrole

Title product of the preceding Preparation (3.5 g, 0.0085 mole) and CuCN (3.05 g, 0.034 mole) were combined with quinoline (30 ml) and the mixture refluxed 4.5 hours, then cooled, poured into stirring ethyl acetate and filtered. The filtrate was washed with 2N HCl, water and brine, dried, treated with activated carbon and stripped to dryness. The resulting residue was slurried in ether and filtered to yield title product 1.29 g; m.p. 234°–240°; tlc (4:1 toluene:ethyl acetate) Rf 0.50; ms 269, 242, 140.

PREPARATION 17

N-(p-Iodophenyl)-p-cyanophenacylamine p-Cyanophenacyl iodide (18.0 g, 0.08 mole) was combined with p-iodoaniline (35.2 g, 0.16 mole) in 32.1 g of absolute ethanol and stirred 16 hours. Precipitated title product was recovered by filtration and repulped in 400 ml ether: 42.4 g; m.p. 160°–165°; ms 362, 232, 219.

PREPARATION 18

1-(p-Bromophenyl-2-mercapto-4-(p-cyanophenyl)imidazole

Title product of Preparation 13 (1.49 g, 0.048 mole), concentrated HCl (0.46 g, 0.048 mole), KSCN (0.46 g, 0.047 mole) and 31 ml 95% ethanol were combined and refluxed 1.25 hours. The reaction mixture was cooled and poured into 50 ml H$_2$O containing 0.5 ml concentrated NH$_4$OH. The resulting slurry was granulated 10 minutes and filtered. The filter cake was sucked dry for 10 minutes, then repulped in ether to provide title product: 1.38 g; m.p. 307°–311°; ms 356, 276, 218; tlc (4:1 toluene:ethyl acetate) Rf 0.40.

PREPARATION 19

1-(p-Bromophenyl)-4-(p-cyanophenyl)imidazole

Title product of the preceding Preparation (733 mg, 2.05 mmoles) was slurried in 37 ml CH$_3$CO$_2$H with cooling to 0°–5°. NaNO$_3$ (73 mg, 0.105 mmole) in a mixture of 0.73 ml concentrated HNO$_3$ and 2.2 ml H$_2$O was added and the reaction mixture then warmed to room temperature. After 30 minutes, when dissolution was almost complete, crystallization of product began. After stirring a further 45 minutes, the slurry was poured into ice-water, granulated and filtered. The wet filter cake was repulped in 100 ml 1:1 H$_2$O:concentrated NH$_4$OH, refiltered and water washed to yield title product: 474 mg; m.p. 178°–185°; tlc (4:1 toluene:ethyl acetate). Rf 0.27.

PREPARATION 20

1,4-Di(p-cyanophenyl)imidazole

Title product of the preceding Preparation (400 mg, 1.23 mmoles) and CuCN (414 mg, 4.92 mmoles) were combined in 4 ml DMF and the mixture refluxed 9.5 hours, cooled and poured into 24 ml H$_2$O containing 8 g of NaCN. The resulting slurry was filtered and the dried filter cake repulped in acetone and then in ether yielding 312 mg of solids. Chromatography on silica gel with ethyl acetate as eluant and recovering the less polar component gave purified title product 164 mg; m.p. 258°–263°; tlc (20:1 CHCl$_3$:CH$_3$OH) Rf 0.32.

PREPARATION 21 p-Cyanobenzaldehyde Benzenesulfonylhydrazone

Benzenesulfonyl hydrazine (20.5 g, 0.12 mole) was dissolved by warming in 110 ml absolute ethanol. p-Cyanobenzaldehyde (15.6 g, 0.12 mole) was separately dissolved in 50 ml of hot ethanol and added to the hydrazine solution The resulting slurry was refluxed 0.5 hour, cooled and filtered to yield 28.1 g; m.p. 209°–213°. Recrystallization from CH$_3$CN gave purified title product: 23.7 g; m.p. 210°–213°.

PREPARATION 22

2,5-Di(p-cyanophenyl)tetrazole

Title product of the preceding Preparation (1.55 g, 0.005 mole) was dissolved in 30 ml pyridine and cooled to −5°. A room temperature solution of p-cyanoaniline (0.59 g, 0.005 ml) in a mixture of 1.3 ml concentrated HCl and 13 ml 9:4 H$_2$O:ethanol was added, the mixture was recooled to 0°, and NaNO$_2$ (345 mg, 0.005 mole) in 2 ml H$_2$O was added dropwise over 15 minutes. After stirring an additional 45 minutes at −5° to −10°, the reaction mixture was poured into CHCl$_3$, washed with H$_2$O and then brine, dried, treated with activated carbon, and stripped to solids. The latter were triturated 3x with hexane, and repulped in ether and then acetone to yield title product: 576 mg; m.p. 216° (dec.); tlc (4:1 toluene:ethyl acetate) Rf 0.63.

PREPARATION 23

1,4-Di(p-cyanophenyl)-2-methylimidazole

Title product of Preparation 20 (1.3 g, 0.0048 mole) was stirred with 200 ml dry THF at −78° under N$_2$. t-Butyl lithium (5.8 ml of 1M in pentane, 0.0058 mole) was added dropwise over 3 minutes. After 27 minutes at −78°, methyl iodide (3.4 g, 0.024 mole) in 15 ml THF was added dropwise over 3 minutes. After 2 hours at −78°, additional methyl iodide (1.7 g, 0.012 mole) and then t-butyl lithium (6.6 ml, 0.0066 mole) were added and stirring continued for a few minutes. The reaction was quenched into 1.2 liters $H_2O$ and extracted with ethyl acetate. The organic layer was washed 2× with fresh $H_2O$ and then brine, dried, treated with activated carbon, and stripped to a foam, 1.04 g. The foam was chromatographed on 50 g silica gel, eluting with ethyl acetate: 350 mg; m.p. 212°–220°.

PREPARATION 24

1,4-Di(p-cyanophenyl)-2-(alpha-hydroxybenzyl)-imidazole

Title product of Preparation 20 (1.5 g, 0.0056 mole) was combined with 200 ml dry THF and stirred under $N_2$ at −78°. t-Butyl lithium (4.6 ml of 1.33M in pentane, 0.0062 mole) was added dropwise over 2 minutes, followed after 10 minutes by the dropwise addition of benzaldehyde (1.8 g, 0.0167 mole) in 10 ml THF. After stirring 1.5 hours, the reaction mixture was poured slowly into 500 ml of ice and water, and extracted with ethyl acetate. The extract was washed with $H_2O$ and then brine, dried, treated with activated carbon, stripped to wet solids and triturated with acetone to yield title product: 623 mg; m.p. 217°–222°; tlc (20:1 $CHCl_3:CH_3OH$) Rf 0.39. A second crop was obtained from the acetone mother liquor: 141 mg; m.p. 218°–224°.

PREPARATION 25

1,4-Di(p-cyanophenyl)-2-(alpha-chlorobenzyl)-imidazole

Title product of the preceding Preparation (1 g, 0.0027 mole) was dissolved in 100 ml THF and stirred under $N_2$. $SOCl_2$ (1 ml, 1.58 g, 0.0133 mole) was added and reaction stirred 1.25 hours, then refluxed 1.5 hours, cooled and stripped to a foam. The foam was repulped in cold ether to yield title product: 780 mg; tlc (4:1 toluene:ethyl acetate) Rf 0.19.

PREPARATION 26

1,4-Di(p-cyanophenyl)-2-benzylimidazole

Title product of the preceding Preparation (780 mg, 0.002 mole), tributyltin hydride (1.16g, 0.004 mole) and a few crystals of azobisisobutyronitrile were combined under $N_2$ in 80 ml of toluene and the mixture refluxed 1.5 hours, then stripped to an oil and distributed between 50 ml each hexane and $CH_3CN$. The $CH_3CN$ layer was separated, washed 4× with fresh hexane and stripped to a foam which was chromatographed on 40 g silica gel, eluting with 4:1 toluene:ethyl acetate and monitoring by tlc. Clean product fractions were combined and stripped to yield title product: 280 mg; m.p. 168°–188°; ms 360; ir(KBr) includes 4.5 microns CN peak; tlc (4:1 toluene:ethyl acetate) Rf 0.30.

PREPARATION 27

1,4-Di(p-cyanophenyl)-2-(alpha-hydroxy-2-picolyl)-imidazole

By the method of Preparation 24, title product of Preparation 20 (7.5 g, 0.028 mole) was converted to present title product: 3.3 g; m.p. 167°–175° C.; ir(KBr) includes CN band at 4.5 microns; ms 377; tlc (20:1 $CHCl_3: CH_3OH$) Rf 0.42.

PREPARATION 28

1,4-Di(p-cyanophenyl)-2-(alpha-chloro-2-picolyl-)imidazole Hydrochloride

Title product of the preceding Preparation (1.5 g, 0.004 mole) was dissolved in 100 ml dry THF and cooled to 0°–5° C. $SOCl_2$ (1.4 g, 0.012 mole) was added dropwise. After stirring 0.5 hour at 0° C., the reaction was stripped and the residue repulped in ether to yield title product: 1.4 g; m.p. 140° (dec.); ms 397/395; tlc (20:1 $CHCl_3:CH_3OH$) Rf 0.62.

PREPARATION 29

1,4-Di(p-cyanophenyl)-2-(2-picolyl)imidazole Hydrochloride

By the method of Preparation 26, title product of the preceding Preparation (1.4 g, 0.0032 mole) was converted to present title product; using 20:1 $CHCl_3$ $CH_3OH$ as eluant in the chromatography, and triturating the final product with 20:1 ether:ethyl acetate: 620 mg; m.p. 185–194°; ir(KBr) includes CN band at 4.5 microns; ms 361.

PREPARATION 30

1-(p-Bromophenyl)-2-methylthio-4-(p-cyanophenyl)-imidazole

Title product of Preparation 18 (3.36 g, 0.094 15 mole) and then methyl iodide (0.6 ml, 0.094 mole) were added to 107 ml of 90% ethanol containing 534 mg NaOH. The mixture was refluxed 4 hours, cooled to 0°–5° and title product recovered by filtration: 2.5 g (71%); m.p. 188°–190° ; ms 372/370, 298/296, 182, 171, 169; tlc (4:1 toluene:ethyl acetate) Rf 0.60.

PREPARATION 31

1,4-Di(p-cyanophenyl)-2-methylthioimidazole

By the method of Preparation 16, title product of the preceding Preparation (2.49 g, 0.0067 mole) was converted to present title product: 420 mg; m.p. 209°–219° ms 316, 283, 243, 200, 182.

PREPARATION 32

1-(p-Iodophenyl)-2-mercapto-4-(p-cyanophenyl-)imidazole

By the method of Preparation 18, title product of Preparation 17 (15.0 g, 0.041 mole) was converted to present title product: 7.43 g (44.5%); m.p. 285°–290° ; ms 403, 371, 276.

PREPARATION 33

1-(p-Iodophenyl)-2-propylthio-4-(p-cyanophenyl) imidazole

Title product of the preceding Preparation (4.03 g, 0.01 mole) and 1-bromopropane (3.68 g, 0.03 mole) were combined in 413 ml 90% ethanol containing NaOH (0.44 g, 0.011 mole) and stirred 5.5 hours. The reaction mixture was then filtered and the filtrate stripped. The resulting residue was repeatedly triturated with hexane and distributed between $H_2O$ and ethyl acetate. The organic layer was separated, washed with $H_2O$ and then brine, dried, stripped to an oil, and crystallized by trituration with isopropyl ether to yield title product: 3.06 g; m.p. 110°–115° ; ms 445, 405, 344, 276.

PREPARATION 34

1,4-Di(p-cyanophenyl)-2-propylthioimidazole

Title product of the preceding Preparation (3.12 g, 0.007 mole) and CuCN (2.51 g, 0.028 mole) were combined in 30 ml DMF and heated in an oil bath at 155° for 1 hour. The reaction mixture was cooled, poured into 400 ml saturated KCN, and the precipitated title product granulated and recovered by filtration: 2.28 g; m.p. 117°–122°; ms 344, 302.

PREPARATION 35

1-(p-Iodophenyl)-2-(2-hydroxyethylthio)-4-(p-cyanophenyl)imidazole

By the method of Preparation 33, a like quantity of title product of Preparation 32 and ethylene bromohydrin (2.1 g, 0.017 mole) were converted to present title product: 2.92 g (65.3%); m.p. 148°–172°; ms 447, 403, 217; tlc (1:1 toluene:ethyl acetate) Rf 0.45.

PREPARATION 36

1,4-Di(p-cyanophenyl)-2-(2-hydroxyethylthio)imidazole

By the method of Preparation 34, title product of the preceding Preparation (2.79 g, 0.0062 mole) was converted to present title product: 2.06 g. The initially isolated product was slurried in ethyl acetate to yield a first crop of title product: 257 mg; m.p. greater than 300°; tlc (1:1 toluene:ethyl acetate) Rf 0.36; ms 346, 315, 301, 242. The ethyl acetate filtrate was chromatographed on silica gel with ethyl acetate as eluant to yield additional title product (501 mg) having identical physical properties.

PREPARATION 37

1-(p-Iodophenyl)-2-(2,3-dihydroxypropylthio)-4-(p-cyanophenyl)imidazole

By the method of Preparation 33, title product of Preparation 32 (4.5 g, 0.011 mole) and 3-chloro-1,2-propandiol (1.48 g, 0.013 mole) were converted to present title product. After stripping the reaction mixture, the residue was simply repulped in water: 517 g; m.p. 160°–174°; ms 477, 446, 403; tlc (1:1 toluene:ethyl acetate) Rf 0.20.

PREPARATION 38

1,4-Di(p-cyanophenyl)-2-(2,3-dihydroxypropylthio)imidazole

By the method of Preparation 34, title product of the preceding Preparation (5.0 g, 0.0105 mole) was converted to present title product. The product initially isolated was further pruified by stirring with 200 ml acetone, removing 1.28 g of insoluble material, and stripping the filtrate to 2 g of solids. The latter were redissolved in acetone and chromatographed on silica gel with ethyl acetate as eluant to yield purified title product: 368 mg; m.p. 190°–195°; tlc (1:1 toluene: ethyl acetate) Rf 0.14.

PREPARATION 39

1-(p-Bromophenyl)-2-(3-picolylthio)-4-(p-cyanophenyl)imidazole

NaOH (0.96 g, 0.024 mole) was dissolved in 98 ml 98% ethanol. Title product of Preparation 18 (3.0 g, 0.0084 mole) was added, followed by 3-picolyl chloride hydrochloride (1.61 g, 0.0092 mole). After stirring for 10 minutes, just as there was almost complete solution, heavy precipitation began. After 1 hour, title product was recovered by filtration, with water repulp: 3.03 g; m.p. 177°–178°; ms 447, 298, 259; tlc (1:1 toluene:ethyl acetate) Rf 0.4.

PREPARATION 40

1,4-Di(p-cyanophenyl)-2-(3-picolylthio)imidazole

By the method of Preparation 34, title product of the preceding Preparation (3.0 g, 0.0067 mole) was converted to present title product: 2.2 g, which was further purified by chromatography on 100 g silica gel using CHCl as eluant: 0.87 g; m.p. 218°–225°; ms 393, 360; tlc (1:1 toluene:ethyl acetate) Rf 0.23.

PREPARATION 41

1-(p-Iodophenyl)-2-(4-picolylthio]-4-(p-cyanophenyl)imidazole

Title product.of Preparation 32 (4.03 g, 0.01 mole) and then 4-picolyl chloride hydrochloride (2.55 g, 0.014 mole) were added with stirring to 413 ml 90% ethanol containing NaOH (1.12 g, 0.028 mole). After stirring 4 hours, the reaction mixture was filtered and the filtrate evaporated to dryness in vacuo. The residue was repulped in ether, taken up in ethyl acetate, washed with water and then brine, dried, treated with activated carbon and restripped to yield title product: 2.96 g (59.9%); m.p. 155°–162°; ms 494, 401, 344, 293, 275, 259.

PREPARATION 42

1,4-(p-Cyanophenyl)-2-(4-picolylthio)imidazole

By the method of Preparation 34, title product of the preceding Preparation (2.34 g, 0.0047 mole) was converted to present title product: 1.02 g; m.p. 170°–174°; ms 393, 360, 301, 259, 243.

PREPARATION 43

1-(p-Iodophenyl)-2-(2-picolylthio)-4-(p-cyanophenyl)imidazole

By the method of Preparation 41, a like quantity of title product of Preparation 32 and 2-picolyl chloride hydrochloride (2.13 g, 0.012 mole) were converted to present title product. After stripping the reaction mixture to dryness and taking up in ethyl acetate and water, a first crop of title product, 897 mg, was recovered by filtration. The ethyl acetate layer in the filtrate was separated, washed with brine, dried and stripped. The residue was repulped in 2-propanol and then chromatographed on silica gel, with ethyl acetate as eluant. The less polar product fractions were combined and stripped to yield a second crop of the product: 714 mg; m.p. 180°–184°; tlc (1:1 toluene: ethyl acetate) Rf 0.53; ms 494, 259.

PREPARATION 44

1,4-Di(p-cyanophenyl)-2-(2-picolylthio)imidazole

By the method of Preparation 34, title product of the preceding Preparation (1.5 g, 0.003 mole) was converted to present title product: 1.36 g, further purified by dissolving in 200 ml of acetone, treating with activated carbon and restripping: 1.05 g; m.p. 164°–170°; ms 393, 360, 307, 270; tlc (1:1 toluene: ethyl acetate) Rf 0.43.

PREPARATION 45

1-(p-Bromophenyl)-2-benzylthio-4-(p-cyanophenyl)imidazole

By the method of Preparation 30, title product of Preparation 18 was converted to present title product.

PREPARATION 46

1,4-Di(p-cyanophenyl)-2-(benzylthio)imidazole

By the method of Preparation 34, title product of the preceding Preparation was converted to present title product, initially obtained as gummy solids. The latter were taken up in acetone, filtered and the filtrate chromatographed on silica gel to yield purified title product: 766 mg; m.p. 168°-172° C.; ms 392, 360, 258.

PREPARATION 47

4-Cyano-2-nitrotoluene

With stirring, concentrated H (205 ml) was cooled to 5° C. Keeping the temperature below 20° C., concentrated $HNO_3$ (85 ml) was added dropwise. Keeping the temperature below 40° C., p-tolunitrile (96 ml) was then added dropwise. After stirring 10 minutes, the reaction mixture was quenched onto 3 kilograms ice, granulated and filtered to yield title product: 120.5 g; m.p. 102°-104°.

PREPARATION 48

1-(p-Cyanophenyl)-2-(o-nitro-p-cyanophenyl)ethanol

Title product of the preceding Preparation (122.4 g, 0.755 mole) and p-cyanobenzaldehyde (100.0 g, 0.755 mole) were dissolved in 882 ml DMSO. $NaOCH_3$ (6.125 g, 5 mole) was added and the mixture stirred 4 hours, then quenched into 6 liters of ice and water, granulated 1 hour and title product recovered by filtration: 201.3 g; m.p. 147°-153°.

PREPARATION 49 p-Cyano-o-nitrobenzyl p-Cyanophenyl Ketone

Title product of the preceding Preparation (100.7 g, 0.343 mole) in 2.5 liters acetone at 5° was oxidized with $CrO_3$ in pyridine (132 ml of 0.343 M) added dropwise over 20 minutes. The reaction mixture was stripped, the residue repulped in water at 70° to yield title product: 93.5 g. The latter was further purified by dissolution in 650 ml warm $CH_3CN$, treatment with activated carbon, evaporation to 250 ml, cooling and filtration: 69.9 g; m.p. 188°-190°.

PREPARATION 50

2-(p-Cyanophenyl)-6-cyanoindole

Title product of the preceding Preparation (28.5 g, 0.097 mole) was combined with 700 ml $CH_3CO_2H$ and stirred at 0°-5° C. while zinc powder (64.0 g, 0.097 mole) was added portionwise. The mixture was then refluxed 45 minutes and filtered hot. The mixture was reduced in volume by stripping, cooled and crude product recovered by filtration. The latter was slurried for 0.5 hour in 5% $NaHCO_3$, recovered by filtration, taken up in acetone and the mixture filtered and the cake washed with acetone until the wash was free of yellow color. The combined filtrate and wash were stripped to yield purified title product: 20.7 g; m.p. 270°-275°.

I claim:

1. A compound of the formula

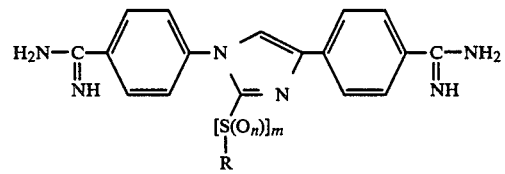

wherein
n is 0, 1 or 2;
m is 0 or 1;
R is $(C_1-C_3)$alkyl, 2-hydroxyethyl, 2,3-dihydroxypropyl, benzyl or 2-, 3- or 4-picolyl; with the provisos that when R is 4-picolyl, m is 1; and when R is methyl and m is 1, n is other than 0;
or a pharmaceutically acceptable salt thereof.

2. The compound of claim 1 wherein n and m are each 0 and R is methyl.

3. The compound of claim 1 wherein n is 0, m is 1 and R is 4-picolyl.

4. The compound of claim 1 wherein n is 0, m is 1 and R is 2-hydroxyethyl.

5. A pharmaceutical composition suitable for parenteral administration in the treatment of a protozoal infection in a mammal which comprises an antiprotozoal effective amount of a compound of claim 1 and a pharmaceutically acceptable liquid vehicle.

6. A method of treating a susceptible protozoal infection in a mammal which comprises parenteral administration of an antiprotozoal effective amount of compound of claim 1 in a pharmaceutically acceptable liquid vehicle.

* * * * *